United States Patent [19]

Kaiho et al.

[11] 4,199,548

[45] * Apr. 22, 1980

[54] THERMALLY DIFFUSIBLE COMPOSITES

[75] Inventors: Keisuke Kaiho; Risaburo Yoshida; Yusaku Ide; Takeshi Hirose, all of Kyobashi, Japan

[73] Assignee: Toyo Ink Manufacturing Co., Ltd., Tokyo, Japan

[ * ] Notice: The portion of the term of this patent subsequent to Jun. 6, 1995, has been disclaimed.

[21] Appl. No.: 900,558

[22] Filed: Apr. 27, 1978

[30] Foreign Application Priority Data

Jun. 10, 1977 [JP] Japan .................................. 52/67817
Jun. 16, 1977 [JP] Japan .................................. 52/70513
Dec. 20, 1977 [JP] Japan .................................. 52/152370

[51] Int. Cl.² ............................ F24J 1/00; F24J 3/00; A61K 9/72; A01N 17/04

[52] U.S. Cl. .................................... 422/305; 43/125; 44/3 B; 44/3 C; 44/39; 252/67; 422/126; 422/239; 424/40

[58] Field of Search ............... 422/305, 306, 125, 126, 422/239; 252/67, 70; 44/39, 3 C, 3 B; 126/263; 424/40; 43/125

[56] References Cited

U.S. PATENT DOCUMENTS

| | | | |
|---|---|---|---|
| 863,933 | 8/1907 | McLaren | 422/305 X |
| 1,819,145 | 8/1931 | Beck | 422/305 X |
| 2,120,204 | 6/1938 | Langhurst | 422/305 X |
| 2,497,612 | 2/1950 | Katzman | 422/125 |
| 2,546,964 | 4/1951 | Blackford et al. | 422/305 X |
| 2,557,815 | 6/1951 | Wheelunght et al. | 422/305 X |
| 2,590,529 | 3/1952 | Gillies et al. | 422/29 X |
| 2,682,461 | 6/1954 | Hutchison | 424/40 X |
| 3,039,921 | 6/1962 | Brandenberg et al. | 424/40 |
| 3,301,250 | 1/1967 | Glasser | 126/263 |
| 3,304,161 | 2/1967 | McGoff | 44/39 X |
| 3,311,459 | 3/1967 | Francis et al. | 44/3 R |
| 3,723,615 | 3/1973 | Okuno | 424/40 X |
| 3,804,771 | 4/1974 | Margolis | 126/236 X |
| 3,856,933 | 12/1974 | Jankowiak et al. | 424/40 X |
| 3,911,101 | 10/1975 | Okuno | 424/40 |
| 4,093,424 | 6/1978 | Yoshida et al. | 44/3 C |

FOREIGN PATENT DOCUMENTS 46-28119 8/1971 Japan .......................... 424/40

Primary Examiner—Barry S. Richman
Attorney, Agent, or Firm—Frank J. Jordan

[57] ABSTRACT

A thermally diffusible composite comprising a thermally diffusible medicine such as allethrin, a thermogenic composition including an alkali metal sulphide or the like, carbonaceous material or the like and, if desired, a filler such as cellulose. In one embodiment, this invention relates to such a thermally diffusible composite the thermogenic composition or the whole of which is enclosed in an oxygen-impermeable container.

34 Claims, 11 Drawing Figures

THERMALLY DIFFUSIBLE COMPOSITES

This invention relates to a novel thermally diffusible composite for expelling or exterminating noxious organisms and more particularly it relates to such a composite characterized by containing as the heat source a thermogenic composition capable of generating heat upon contact with air or oxygen.

Conventional thermally diffusible composites such as conventional smoking or fumigating composites, comprise a thermally diffusible medicine for expelling or exterminating noxious organisms (the medicine being hereinafter referred to as "effective medicine" for brevity), as well as a combustible material, oxidizer, stabilizer and like material; when used, they are ignited to burn the combustible material thereby to thermally diffuse the effective medicine in the atmosphere.

However, the conventional diffusion method using such burning or combustion is disadvantageous in that the temperature obtained by the use of such burning is generally high and very difficult to control while the effective medicines vary in diffusion temperature depending on the kind thereof and have their respective optimum diffusion temperatures, whereby the effective medicines are pyrolyzed and consequently reduced in medicinal effect, accompanied with adverse effects of gases produced by the pyrolysis and combustion on containers in which the thermally diffusible composite is present.

Thus, in the preparation of the conventional such composites, it is required to select effective medicines which are resistant to the combustion temperature of the combustible material thereby preventing the pyrolysis of the effective medicine or else to use combustible material capable of combustion at lower temperatures or additionally use a combustion adjusting agent; however, even in this case, the temperature obtained by the combustion cannot be controlled to a satisfactory extent, poisonous gases are produced and the composites so improved increase in production cost, whereby the disadvantages of the conventional composites are not fundamentally nor thoroughly solved. The conventional composites are further disadvantageous in that they need a fire source when used and tend to cause fires and scald accordingly, thus raising problems as to safety.

Thermally diffusible composites using electricity as the heat source are also known, however, they are generally impossible to make wide uses of since they cannot be used in areas other than those in which electricity is available.

In order to solve the aforementioned problems of the conventional thermally diffusible composites, there have recently been proposed methods for diffusing the effective medicine by heating with a chemical thermogenic agent and they have solved the problems to some extent.

However, the conventional thermally diffusible composites in which the conventional thermogenic agent is used will not exhibit satisfactory diffusion of the effective medicine when heated. The heretofore proposed thermogenic agents require oxygen and a considerable amount of water to commence heat generation and endure it thereby making the operation of use of the thermogenic agents complicated; in addition, these proposed agents are defective in that they cannot fully diffuse the effective medicine when used for smoking and thermally fumigating the medicine in a short time since the amount of heat generated by them is considerably small as compared with that of the thermogenic composition of this invention. Further, the conventional composites are not of such a structure as to efficiently transmit the heat produced by the thermogenic agent to the effective medicine.

The novel thermally diffusible composites of this invention eliminate the aforesaid disadvantages of the conventional ones and they comprise the effective medicine and the thermogenic composition which starts heat generation just only by contact with the oxygen in air and endure it for a long time without supply of water and the like to the composition during the operation and which may be controlled to generate heat so that the temperature obtained by the heat generation varies from a low temperature to a high one as desired.

The term "thermally diffusible" used herein is intended to mean "capable of fumigation, volatilization, vaporization, gasification, sublimation or the like when heated".

This invention will be detailed hereinbelow.

The effective medicines used in this invention may be any one which is diffusible by being heated, and they include insecticides, attractants, expellents, rodenticides, cockroachicides and fungicides. More particularly, the insecticides include pyrethroid such as allethrin and phthalthrin (N-(3,4,5,6-tetrahydrophthalimido)-methyl chrysanthemumate); organic phosphorus compounds such as DDVP, fenitrothion and diazinon; organic chlorine compounds such as lindane and chlordane; and insect metamorphosis hormones such as carbamate compounds. The attractants include 10,12-hexadecadiene-1-o1 and amino acids, the expellents include dimethyl phthalate and N,N-diethyltoluamide (DET), and the fungicides include Naramycine (cycloheximide), thiuram, 2,3-dichloro-1,4-naphthoquinone (dichlone) and chlorobenzilate.

In case where the effective medicine used is pyrethroid for example, there may additionally be used various adjuvants such as S-421 (octochlorodipropyl ether), MGK 264, piperonyl butoxide and synepirin 500 to increase the efficacy of the pyrethroid.

There may be used various effective medicines in the practice of this invention and, among other things, pyrethloid type insecticides are known as those which have high medicinal efficacy and have low toxicity to human bodies.

The pyrethloid type insecticides may more particularly be illustrated by:

3-allyl-2-methylcyclopenta-2-ene-4-on-1-yl dl-cis, trans-chrysanthemumate (hereinafter referred to as "allethrin"), 3-allyl-2-methylcyclopenta-2-ene-4-on-1-yl d-cis, trans-chrysanthemumate (hereinafter referred to as "d-cis-trans-allethrin"), d-3-allyl-2-methylcyclopenta-2-ene-4-on-1-yl d-trans-chrysanthemumate (hereinafter referred to as "d,d-trans-allethrin"), 3-phenoxybenzyl d-cis, trans-chrysanthemumate (hereinafter referred to as "phenothrin"), 3-phenoxybenzyl dl-cis, trans-3-(2,2-dichlorovinyl)-2,2-dimethyl-1-cyclopropanecarboxylate (hereinafter referred to as "permethrin"), 5-benzyl-3-furylmethyl dl-cis, trans-chrysanthemumate (hereinafter referred to as "Resmethrin").

Using these pyrethroid type insecticides, there may be prepared thermally diffusible composites of this invention for effectively exterminating insects.

The thermogenic compositions producing heat by contact with oxygen or air according to this invention consist essentially of (A) at least one member selected from the group consisting of alkali metal sulphides, polysulphides, hydrosulphides and hydrates thereof and (B) at least one material which exhibits a catalytic function when the component (A) generates heat by contact with oxygen or air. The component (A) includes the sulphide, polysulphide or hydrosulphide of an alkali metal such as Li, Na, K, Rb or Cs, or the hydrate thereof, each in powder form; one or more of these compounds may be used as the component (A). Among the alkali metals, Na and K are preferable with Na being more preferable. The aforesaid compounds as the component (A) are thermally stable without generation of heat when mixed, in air, with the component (B) such as carbon black or other carbonaceous material to be described later.

The component (B) is at least one member selected from the group consisting of (1) carbonaceous materials, (2) iron carbide, (3) activated clay, etc. The carbonaceous materials and iron carbide are preferred from the thermogenic point of view.

The carbonaceous materials include carbon black, activated carbon, charcoal, coke, pitch, asphalt, graphite and soot, with carbon black, activated carbon and charcoal being particularly preferred from the viewpoint of their high surface activity and catalytic activity on the heat generation of the component (A).

The component (B) may also be a carrier, such as an asbestos carrier, to which the aforesaid carbonaceous material is attached.

The iron carbide is such that the present inventors already developed a process for the production thereof and made a Japanese application for a patent on the process (Japanese Patent Application Laying-Open Gazettes Nos. 22000/75, 45700/76 and 116397/75); it is obtained by pyrolyzing prussian blue in an inert or non-oxidizing atmosphere. In addition, as the component (B) activated clay or the like may be used alone or jointly with another material for the component (B).

Furthermore, the component (B) may be used jointly with at least one of iron, nickel and cobalt sulphates, their hydrates and anthraquinone sulphonate derivatives such as 1,8-anthraquinone-disulphonic acid dipotassium salt.

The components (A) and (B) are not specifically limited in particle size, exhibit better thermogenic effects as they are smaller in particle size and are preferably used in particle size of 10 mesh or finer.

The thermogenic mechanism of the thermogenic compositions of this invention is not necessarily clear but supposed such that the component (A) is oxidized with oxygen in the presence of the component (B) having an oxidizing catalyst-like function thereby generating oxidation heat as the heat source. This supposition is based on the fact that the compound (A) does not generate heat for itself in air but generates heat by being mixed with the component (B) and that sulphate or thiosulphate radicals are detected in a large amount by analysis for the exothermic reaction product of the components (A) and (B). Accordingly, the amount of heat (cal/g) to be produced from the thermogenic composition according to this invention may be varied as desired by, for example, varying the blending ratio between the components (A) and (B). It is preferable that the component (A) be contained in an amount of 10-90% by weight in the thermogenic composition.

When used, thermogenic compositions containing less than 10% by weight of the component (A) will not produce a satisfactory amount of heat, while those containing more than 90% by weight thereof will decrease in thermogenic or heat-generating efficiency because of unsatisfactory contact with the component (B).

The velocity and duration of heat generation of the thermogenic composition may be controlled as desired by varying the area of contact of the composition with air or oxygen, more particularly by varying the particle size of the components (A) and (B), the amount of air contacting with the composition and the kind and amount of fillers to be described below.

The fillers (component (C)) function as a heat buffer or retainer or the like which inhibits abrupt changes in temperature due to heat generation or radiation. They may preferably have porosity, good air-permeability and low specific gravity; they include wood dust; cotton linter; natural fibers in fragmentary form such as cellulose; synthetic fibers in fragmentary form such as polyester fibers; synthetic resin foams in fragmentary form such as polystyrene and polyurethane foams; and inorganic materials such as silica powder, porous silica gel, sodium sulphate, calcium sulphate, sodium carbonate, barium sulphate, iron oxides, aluminum oxide and asbestos. In addition, adjuvants for molding may be used if the molding is necessary. These materials as the component (C) may be used in the ratios by weight of from 0/100 to 90/10, preferably from 20/80 to 70/30 between the component (C) and the total of the components (A) and (B).

The oxygen sources used in this invention may be air which is the most convenient and inexpensive and may also be pure oxygen and a compound capable of producing oxygen by a chemical reaction thereof.

The thermogenic compositions used in this invention, when used, will give a temperature of about 1000° C. at highest, and the temperature obtained and duration thereof may be controlled in any desired way as previously mentioned. For example, a temperature of about 250°–500° C. may be used for heating comparatively heat-stable medicines such as DDVP and diazinon, while a temperature of about 200° C. may be used for heating thermally unstable medicines such as pyrethroid type insecticides. For insects, such as cockroaches, which will escape to a place where the effective medicine is not present when the effective medicine is slowly fumigated over a long period of time, a desired dose of the effective medicine is necessary to rapidly smoke or fumigate in a short time such as about 5–15 minutes by, for example, increasing the amount of air contacting with the thermogenic composition thereby increasing the amount of heat produced.

In this invention, the thermally diffusible composites may of course contain a conventional paste, colorant, color coupler, stabilizer and the like in addition to the effective medicine and thermogenic composition.

The structure of the thermally diffusible composite of this invention may widely vary and will be illustrated by the accompanying drawing in which.

The term "wrap or enclose" used herein is intended to mean "airtightly or substantially airtightly wrap or enclose".

Figure 1:
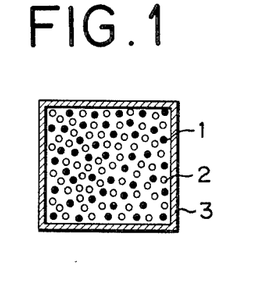
FIGS. 1–3 are each a cross-sectional view of a wrapped thermally diffusible composite embodying this invention.

(1) Referring to FIG. 1, the effective medicine 1 and thermogenic composition 2, each in particulate, powdery or granular form, are mixed together in a certain ratio to obtain a uniform mixture, and the mixture so obtained is then enclosed in a metallic container or an oxygen-impermeable bag 3 to obtain a thermally diffusible composite in enclosed state of this invention.

Figure 2:
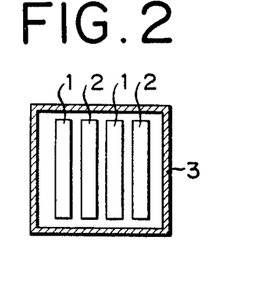

(2) Referring to FIG. 2, the effective medicine 1 and thermogenic composition 2 are molded to obtain their respective moldings which are then enclosed in a metallic container or a suitable oxygen-impermeable bag, thereby obtaining a composite in enclosed state of this invention. Moldings obtained from a mixture of the medicine 1 and composition 2 may be used in substitution for the former moldings.

Figure 3:
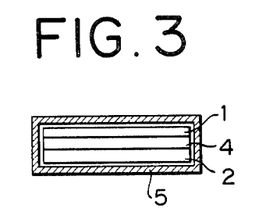

(3) Referring to FIG. 3, a sheet-like or foil-like metal is laminated at one side with a molded effective medicine 1 or with a porous sheet, such as paper, impregnated with the effective medicine 1 and also laminated at the other side with a molded thermogenic composition 2, and the whole is then enclosed in an oxygen-impermeable sheet 5 to obtain a composite in enclosed state of this invention. The aforesaid structure in which the effective medicine and thermogenic composition are not directly contacted with each other, is desirable in ensuring the stability of each of the medicine and composition.

In said cases (1) and (2), it is desirable that the material of the effective medicine and that of the thermogenic composition be such that both of the materials have no effects on each other.

In the case (2), for example a powdery or granular thermogenic composition is put in a container, preferably a heat resistant container, and an effective medicine-impregnated porous carrier is placed on the thermogenic composition, after which the whole is then enclosed in an oxygen-impermeable container or the like; otherwise, the effective medicine-impregnated porous carriers and the thermogenic composition moldings may be laminated alternately with each other and then enclosed in such a container or the like. These carriers and moldings may be laminated with the use of an adhesive, preferably a heat resistant adhesive, if necessary.

In connection with the case (3), a thermally diffusible composite having a more advantageous structure will be described hereinbelow. This preferable composite is prepared by forming a layer of a thermally diffusible effective medicine for expelling noxious organisms on the outer side of a metallic container provided on the wall thereof with an opening, placing the thermogenic composition in the container, covering the opening with a filter which does not allow the thermogenic composition to pass therethrough but is permeable to oxygen and then covering only the opening with, or enclosing the whole of the container in, an oxygen-impermeable sheet or molding.

Figure 4:
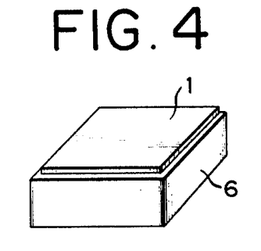
FIGS. 4–7 are each a perspective view of a thermally diffusible composite embodying this invention prior to being wrapped.
Figure 5:
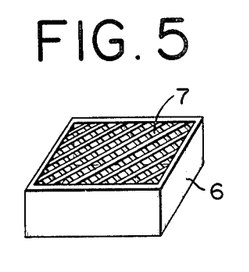
Figure 6:
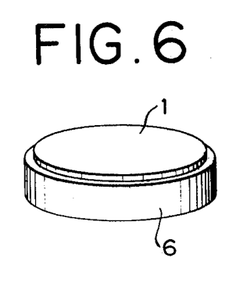
Figure 7:
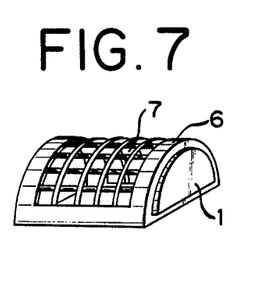
Figure 8:
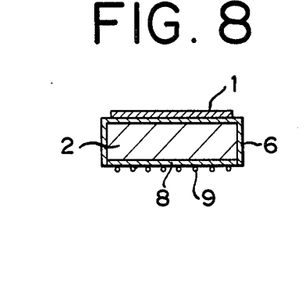
FIG. 8 is a cross section taken through a plane bisecting of FIG. 4.
Figure 9:
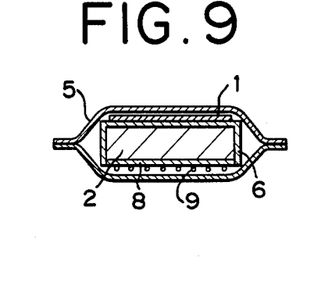
FIG. 9 is a cross-sectional view of an embodiment of thermally diffusible composite in which the thermogenic composition is enclosed in a metallic container, the composite being wholly wrapped in an oxygen-impermeable sheet.

The aforesaid preferable composite will be further explained hereunder by reference to FIGS. 4–6 each showing a perspective view of the preferable composite prior to being enclosed. FIG. 5 is a perspective view showing the reverse side or bottom of FIG. 4 provided with openings. This invention is not limited to the embodiments shown in FIGS. 1–11 as is apparent from the following description.

A metallic container 6 having one or more openings 7 may be used as the container for the thermogenic composition, and it may have, for example, a circular, square, triangular or semi-circular shape in cross section and may also have a combination of these shapes. The container 6 has at least one opening 7 as mentioned above. The opening or openings 7 are not particularly limited in size and shape, however, they must be such that they permit an amount of oxygen or air necessary for the thermogenic composition 2 to pass therethrough. The openings may have a circular semi-circular, square, triangular, hexagonal or like shape and they do not have to be flat. The metallic container 6 is not particularly limited in size, but it may usually be large enough to hold about 50 grams of the thermogenic composition 2 therein.

The metallic container may be made of steel, stainless steel, aluminum or the like and may also be made of a metal-other inorganic material or metal-heat resistant organic material multi-layer laminate although one of the layers must be metallic. It is preferable that the container 6 be made of a material having good heat conductivity. The container 6 is not particularly limited in thickness, but it is usually 0.1–1.0 mm in thickness or may be so thick as to be flexible.

A layer of the effective medicine 1 is formed by (I) a method comprising impregnating a porous carrier with the effective medicine and allowing the thus-impregnated carrier to adhere to a substrate such as a metallic container 6 containing the thermogenic composition 2 (Alternatively, impregnating the porous carrier with the medicine after having been bonded to the container) or by (II) a method comprising dispersing the effective medicine 1 in a coating material which will permit the effective medicine to diffuse therefrom into the atmosphere after dispersion of the medicine 1 in the coating material and formation of a film of the medicine-diffused coating material, and coating the medicine-dispersed coating material on a substrate such as a metallic container containing the thermogenic composition 2. There may be used any methods for forming a film from which a necessary amount of the effective medicine can diffuse into the atmosphere by being heated with the heat produced by the thermogenic composition.

The porous carriers to adhere to the container in the aforesaid method (I) should be those which may retain the effective medicine stably therein and will permit the medicine to diffuse effectively therefrom when heated.

The porous carriers include pulp-made plates, glass fibers, asbestos, porous resins, paper, biscuit plates and porous metals. They are not particularly limited in shape and thickness, however, they may preferably be 2 mm or less in thickness. If they are undulating in shape, their thickness may preferably be 2 mm or less on the average. They may, of course, be varied in thickness depending upon the kind of the effective medicine, etc. The use of porous carriers having a thickness of larger than 2 mm will result in unsatisfactory transfer of heat from the thermogenic composition to the effective medicine in the carrier spaced from the composition thereby causing a tendency of the effective medicine to be hindered from rapid diffusion with the result that the efficiency of diffusion of the effective medicine may decrease and the ratio of decomposition thereof may increase.

The porous carriers consist of one plate-like material or an assembly of smaller plate-like materials for example. They may preferably have an area of 10–500 cm² and may usually be attached to the metallic container with the use of an adhesive. As the adhesive, any ones will be used if they can keep the carrier attached to the container during the transportation of the thermally diffusible composite or the thermal diffusion thereof. Any adhesives will be used herein so long as they do not peel off the container even if they, per se, are carbonized or decomposed by being heated. It is undesirable to use adhesives which will produce a poisonous or offensive odor. The adhesives used herein may be an organic or inorganic material and illustrated by epoxy resins, silicone resins and water-glass.

The preferable coating materials used in the aforesaid method (II), are those which will form a porous film when coated. Further, it is effective to use a coating material, such as paraffin wax, lanolin or petrolatum, which can form a film at ambient temperature and will facilitate the diffusion of the effective medicine as a diffusion medium when used therewith.

The effective medicine layer according to this invention may be incorporated with other ingredients such as a diffusion adjuvant. The diffusion adjuvants used herein include the aforementioned agents for increasing the efficacy of the effective medicine, such as S-421, MGK 264, piperonyl butoxide and synepirin 500; penetrants for facilitating the penetration of the effective medicine into harmful organisms; and antioxidants. The diffusion adjuvants may be suitably be selected depending on the kind or nature of the effective medicine used. For example, in a case where a pyrethroid type effective medicine is used, there may additionally be used penetrants such as isopropyl myristate, and antioxidants such as 2,6-di-tert.-butyl-4-methylphenol (BHT), erythorbic acid and n-propyl gallate.

The thermogenic composition according to this invention should be filled in a metallic container 6 so that the composition contacts with the inner side thereof to increase the efficiency of heat transfer to the effective medicine. It is desirable that a particular consideration of heat efficiency be given to at least the portion of the container on which the effective medicine is placed.

In the metallic container used herein, the opening 7 is covered with a filter 8 to prevent leak of the thermogenic composition therethrough and permit entrance of oxygen or air therethrough into the container. The filter 8 is permeable to gases, but does not permit the thermogenic composition 2 to pass therethrough. Further, it is preferable that the filter be resistant to heat. The materials for the filter 8 include inorganic fibers such as glass fibers, carbon fibers, asbestos, ceramic fibers and metal fibers as well as organic fibers such as polyamide and polyimide resin fibers; they also include polyester fibers unless they are required to have high heat resistance. The filter 8 may be made of one or more layers; for example, one of two layers used is a fibrous one for controlling permeability to gases and preventing leakage of the thermogenic composition, and the other is a metallic net 9 for reinforcing the mechanical strength of the two-layer filter. The rate of flow of air into the thermogenic composition 2 may vary depending on the kind thereof and is in the range of about 10–50 seconds/100 ml (densometer).

Figure 10:
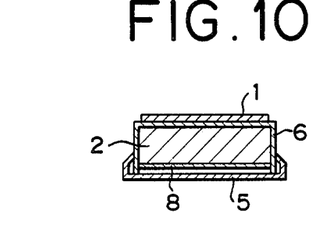
FIG. 10 is a cross-sectional view of another embodiment of a thermally diffusible composite in which the thermogenic composition is enclosed in a metallic container, the container being sealed up by a molding.

The metallic container 6 holding the thermogenic composition 2 therein and having a layer of the effective medicine 1 formed on the outer side thereof, is enclosed thereby to make the whole impermeable to oxygen or air. The container 6 may be wholly wrapped in a bag made of an oxygen-impermeable sheet or in a molding made of an oxygen-impermeable material (FIG. 9) or may be covered only at the filter portion 3 with such a sheet or molding (FIG. 10). The material for the oxygen-impermeable sheet or molding may be a plastic material such as polyethylene, polypropylene, polyvinyl chloride, polyvinylidene chloride, polyester, Nylon or polyvinyl alcohol and may also be a foil or sheet of a metal such as aluminum or steel. The gas-permeable sheet may be laminated with a gas-impermeable sheet for use as the oxygen-impermeable sheet, and the metallic foil may usually be used in combination with a plastic sheet. The thermally diffusible composites as shown in FIGS. 4–10 are easy to handle and excellent in diffusion rate or insecticidal power.

Methods for unwrapping the thermally diffusible composites are illustrated below.

The thermally diffusible composites wrapped in an oxygen-impermeable sheet or molding can easily be placed in condition for use by removing the sheet or molding; they can be unwrapped or opened by means of an "easy to open" mechanism such as a pull-tab if they are provided with it on the wrap; they can be unwrapped by peeling off an oxygen-impermeable cover film if they have an opening for oxygen or air and the cover film covering the opening; they can be unwrapped or opened by means of a threaded opening mechanism (screw-cap, etc.) if they possess it. However, these unwrapping or opening methods should not be such that they hinder the thermogenic composition and effective medicine from generating heat and thermal diffusion, respectively.

Figure 11:
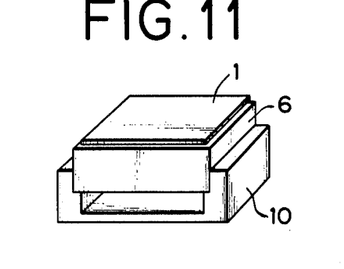
FIG. 11 is a perspective view of the thermally diffusible composite of FIG. 9 or 10 when in use after removal of the oxygen-impermeable sheet or the molding.

The thermally diffusible composites may be put to practical use only by removal of the oxygen-impermeable wrapper or molding, and the composites so unwrapped may be supported on a suitable holder 10 for practical use (FIG. 11).

Further, it is desirable that, as previously mentioned, the container for holding the thermogenic composition therein and supporting the effective medicine on the outer side thereof as well as the material for wrapping the thermally diffusible composite should be heat resistant and adiabatic since the composite is raised in temperature to about 100°–500° C. when in use. The material for the container and wrapper includes a metal, glass cloth, asbestos, heat resistant plastics and paper.

The thermogenic compositions described in the above are those containing the components (A) and (B) in admixture and, if necessary, they may contain the two components in the separate state which will be mixed together when in use.

This invention will be better understood by the following examples wherein all parts are by weight unless otherwise specified.

EXAMPLE 1

(1) Twenty (20) parts of kaolin (average particle size: 10μ) were impregnated with 5 parts of DDVP and then pulverized into a powder which passed through a 100 mesh screen (W. S. Tyler Standard).

(2) Five (5) parts of anhydrous sodium sulphide (average particle size: 100μ), 5 parts of carbon black (particle size: 16 nm), 10 parts of sodium bicarbonate (average particle size: 100μ) and 5 parts of calcium stearate (average particle size: 1μ) were mixed together to form a mixture. The powder (1) so obtained and the mixture (2) so formed were blended together to form a blend which was molded into granules having a particle size of 10 mesh and then enclosed in a metallic container to obtain a thermally diffusible composite in enclosed state. These treatments were all carried out in a nitrogen stream. The enclosed thermally diffusible composite was then disclosed or opened in air whereby it generated heat to the extent that a temperature of 250°–280° C. was reached by said heat generation and at least 95% of the DDVP was diffused in 5 minutes.

COMPARATIVE EXAMPLE 1

The procedure of Example 1 was followed except that 5 parts of iron powder (average particle size: 50μ) and 1 part of ferrous sulphate as the thermogenic composition were used thereby to obtain a thermally diffusible composite in enclosed state. The enclosed composite so obtained was disclosed or opened and simultaneously incorporated with 2 parts of water whereby the thermogenic composition generated heat and rose in temperature to 100°–110° C. thus rendering diffusion of the DDVP substantially impossible.

EXAMPLES 2–8

The procedure of Example 1 was followed except that there were used the effective medicines indicated in the following Table 1 and the following thermogenic compositions. The results are shown in Table 1.

| Thermogenic compositions: | Part(s) |
|---|---|
| a. Sodium sulphide pentahydrate (av. particle size: 10 μ) | 4 |
| Carbon black | 1 |
| Cellulose powder (av. particle size: 40 μ) | 5 |
| b. Anhydrous sodium sulphide | 2 |
| Carbon black | 1 |
| Calcium carbonate (av. particle size: 50 μ) | 2 |
| Sodium carbonate (av. particle size: 200 μ) | 2 |
| c. Anhydrous sodium sulphide | 2 |
| Carbon black | 1 |
| Sodium bicarbonate | 2 |
| Magnesium carbonate (av. particle size: 10 μ) | 1 |
| Alumina powder (av. particle size: 100 μ) | 1 |
| d. Anhydrous sodium sulphide | 1 |
| Iron carbide | 2 |
| Kaolin | 2 |
| e. Anhydrous sodium polysulphide (av. particle size: 100 μ) | 1 |
| Carbon black | 1 |
| Sodium bicarbonate | 2 |

Table 1

| Example | Effecive medicine | (Parts) | Thermogenic composition | (Parts) | Temperature obtained (°C.) | Diffusion ratio (%) |
|---|---|---|---|---|---|---|
| 2 | Allethrin | 1 | a | 5 | 150 | 98 |
| 3 | DDT | 1 | b | 5 | 250 | 80 |
| 4 | Diazinone | 1 | b | 10 | 250 | 95 |
| 5 | BHC | 1 | b | 5 | 250 | 80 |
| 6 | Dichlon | 1 | c | 10 | 250 | 90 |
| 7 | Dibrom | 1 | d | 10 | 300 | 88 |
| 8 | Sumithion | 1 | e | 5 | 200 | 90 |

Note:
Each of the aforesaid effective medicines was one which was incorporated with kaolin in the amount five times the weight thereof.

COMPARATIVE EXAMPLE 2

The procedure of Example 2 was repeated except that a thermogenic composition having the same composition as that of Comparative example 1 was used thereby to obtain a comparative thermally diffusible composite in enclosed state. The comparative enclosed composite so obtained was opened and simultaneously incorporated with 2 parts of water for heat generation with the result that it took at least 5 hours to thermally diffuse 95% of the allethrin.

EXAMPLE 9

A tape-like aluminum foil, 20μ thick and 1 cm wide, was laminated at one side thereof with paper impregnated with DDVP in the amount of 5 g/m² of paper and at the other side with a molded thermogenic composition consisting of 5 parts of anhydrous sodium sulphide, 5 parts of carbon black, 10 parts of calcium bicarbonate and 5 parts of calcium stearate. The whole was then wrapped or enclosed in a bag made of an aluminum foil-polyethylene film laminate to obtain a thermally diffusible composite in enclosed state. The enclosed composite so obtained was opened whereby it generated heat and gave a temperature of 250° C. with the result that at least 95% of the DDVP was diffused in 5 minutes.

EXAMPLE 10

The same thermogenic composition as that used in Example 1 and each of pulp-made plates (area: 50 cm²) having the various thicknesses as shown in Table 2 and impregnated with 500 mg of d,d-trans-allethrin, were enclosed in a metallic container to obtain a thermally diffusible composite in enclosed state. These treatments were all carried out in a nitrogen stream. The enclosed composites so obtained were opened and allowed to generate heat for testing for ratios of diffusion and decomposition or non-diffusion (left unchanged) of the allethrin. In the test, the diffusion was effected for 15 minutes at about 250° C. obtained by the generated heat. The results are shown in Table 2.

Table 2

| Thickness (mm) | Diffusion ratio (%) | Decomposition ratio or non-diffusion (%) |
| --- | --- | --- |
| 0.2 | 99.1 | 0.9 |
| 0.5 | 96.5 | 1.3 |
| 1.0 | 93.3 | 2.0 |
| 2.0 | 90.3 | 5.6 |
| 3.0 | 37.1 | 55.2 |
| 4.0 | 21.9 | 67.3 |

EXAMPLE 11

Five hundred (500) milligrams of each of the various pyrethroid type insecticides as indicated in Table 3 were impregnated into a sheet-like bundle of glass fibers having an area of 33 cm$^2$ and thickness of 1 mm and the insecticides were diffused for testing the ratio of diffusion thereof by being heated with the various thermogenic compositions as indicated in Table 3. The results are shown in Table 3.

The thermogenic compositions used were those which were molded under such varying conditions (for example, selectively using starting materials having different particle sizes) as to obtain necessary temperatures by the heat generation thereof.

Table 3

| Thermogenic composition as used in Examples 2–8 | | c | | | b | |
| --- | --- | --- | --- | --- | --- | --- |
| Insecticide \\ Temperature obtained (°C.) | 100 | 200 | 300 | 400 | 500 | |
| d-cis-trans-allethrin | 13 | 98 | 85 | 83 | 42 | |
| Phenothrin | 0 | 11 | 65 | 85 | 55 | |
| Permethrin | 0 | 15 | 53 | 90 | 50 | |
| Resmethrin | 0 | 15 | 62 | 80 | 45 | |

EXAMPLE 12

A pulp-made plate, 50 cm$^2$ in area and 0.5 mm in thickness, was impregnated with each of the various pyrethroid type insecticides in the various amounts as indicated in Table 4 to prepare an insecticide mat. The insecticide mats so prepared were each combined with the thermogenic composition as indicated in Example 11 to obtain thermally diffusible composites which were then tested on german cockroaches for insecticidal performance in a room having a volume of about 33 m$^3$. The results are shown in Table 4.

Table 4

| Insecticide (mg) | | Thermogenic composition and temperature obtained (°C.) | | Diffusion time (min. sec.) | Insecticidal efficacy (%) |
| --- | --- | --- | --- | --- | --- |
| Allethrin, | 1000 | c, | 250 | 15' 39" | 100 |
| d-cis, trans-allethrin, | 500 | c, | 250 | 13' 40" | 100 |
| d,d-trans-allethrin, | 250 | c, | 250 | 11' 32" | 100 |
| Phenothrin, | 500 | b, | 350 | 23' 25" | 100 |
| Permethrin, | 500 | b, | 380 | 25' 12" | 100 |
| Resmethrin, | 800 | b, | 350 | 18' 53" | 100 |

EXAMPLE 13

A sheet prepared by impregnating paper, 0.5 mm thick×90 mm wide×90 mm long, with 500 mg of permetrin, adhered to the outside of the bottom of an 0.12 mm thick iron plate-made box type container, 100 mm×100 mm×20 mm, (as shown in FIG. 4) with the use of a silicone type adhesive. Then, 40 g of a thermogenic composition consisting of 2 parts of anhydrous sodium sulphide, 1 part of carbon black and 1 part of vermiculite (av. particle size: 50μ) were charged into the container through the opening thereof and the opening was covered with a 5 mm thick rock wool mass, after which the rock wool mass was fixed to the container by the use of an iron net of 10 mesh, to obtain a thermally diffusible composite which was then wrapped or enclosed in an aluminum foil-polyethylene film laminate. The aforesaid procedure was carried out in a nitrogen stream.

The composite so wrapped was unwrapped, placed on a holder as shown in FIG. 11 and allowed to diffuse the permetrin at 250° C. obtained by the reaction of the thermogenic composition with the result that at least 95% of the permethrin was diffused in 15 minutes.

EXAMPLE 14

The procedure of Example 13 was followed except that an 0.5 mm thick pulp-made plate and d,d-trans-allethrin were substituted for the paper and the pertmerin, respectively. The result was that at least 95% of the allethrin was diffused in 15 minutes.

EXAMPLE 15–17

The procedure of Example 13 was followed except that the three kinds of the thermogenic compounds and effective medicines as indicated in Table 5 were substituted for those of Example 13.

Table 5

| Example | Thermogenic composition | (Parts) | Effective medicine |
| --- | --- | --- | --- |
| 15 | The same as in Example 4 | The same as in Example 4 | The same as in Example 4 |
| 16 | The same as in Example 6 | The same as in Example 6 | The same as in Example 6 |
| 17 | Anhydrous sodium polysulphide (av. particle size: φμ) | 1 | Dibrom |
| | Iron carbide (av. particle size: 20 μ) | 2 | |
| | Kaolin (av. particle size: 10 μ) | 2 | |

The result is that the temperatures obtained in Examples 15–17 were 250° C., 250° C. and 300° C., respectively, and at least 95% of the effective medicine was diffused in 15 minutes in each of said Examples.

EXAMPLE 18

A mixture prepared by mixing 100 mg of wax and 400 g of allethrin with the use of xylene, was coated to a thickness of 100μ on the outside of the bottom of an 0.15 mm thick aluminum container (130 mm dia.×15 mm height) as indicated in FIG. 6. Then, as in Example 13, the aluminum container was filled with 30 g of the thermogenic composition through the opening thereof. The opening was covered with a 3 mm thick, glass fiber filter and further sealed up with an aluminum lid having an easy-to-open mechanism by the use of a sealer for canning, thereby to obtain a thermally diffusible composite in enclosed state. The enclosed composite so obtained was opened by the use of the easy-to-open mechanism thereby allowing the effective medicine to diffuse with the result that at least 95% of the medicine was diffused in 15 minutes.

EXAMPLE 19

An 0.5 mm thick circular pulp-made plate (dia. 10 mm) impregnated with 100 mg of DDVP adhered to the same container as used in Example 18 with a water-glass type adhesive. The container filled with a thermogenic composition consisting of 2 parts of anhydrous sodium sulphide, 1 part of carbon black and 1 part of alumina. The procedure other than the aforesaid one was effected in the same manner as used in Example 18 thereby to obtain a thermally diffusible composite in enclosed state. The composite so obtained was then allowed in the same manner as in Example 18 to thermally diffuse the effective medicine with the result that at least 95% thereof was diffused at 350° C. in 15 minutes.

REFERENCE EXAMPLE 1

The thermally diffusible composites as obtained in Examples 13, 15 and 19 were tested on german cockroaches for insecticidal performance in a room having a volume of about 30 m³, with the result that they exhibited a mortality of 100% in the range of from 10 to 25 minutes.

REFERENCE EXAMPLE 2

In the same manner as in Reference example 1, the thermally diffusible composites as obtained in Examples 14 and 18 were tested on housflies for insecticidal performance. The result is that the composites exhibited a mortality of 100% in the range of from 10 to 15 minutes.

What is claimed is:

1. A thermally diffusible composite comprising:
   (1) a thermally diffusible medicine for expelling or exterminating noxious organisms and
   (2) a thermogenic composition as the heat source for said thermally diffusible medicine, comprising
   (A) at least one member selected from the group consisting of sulphides, polysulphides and hydrosulphides of alkali metals, and hydrates thereof and
   (B) at least one member selected from the group consisting of carbonaceous material, iron carbide and activated clay.

2. A thermally diffusible composite according to claim 1, wherein the thermally diffusible medicine is a pyrethroid type one.

3. A thermally diffusible composite according to claim 1, wherein the thermally diffusible medicine is a thermally diffusible insecticide, attractant, repellent, rodenticide or fungicide.

4. A thermally diffusible composite according to claim 1 or 3, wherein the alkali metal is at least one member selected from the group consisting of sodium and potassium.

5. A thermally diffusible composite according to claim 1 or 3, wherein the carbonaceous material is at least one member selected from the group consisting of carbon black, activated carbon, charcoal, coke, pitch, asphalt, graphite and soot.

6. A thermally diffusible composite according to claim 1 or 3, wherein the thermogenic composition contains the component (A) in an amount of 10–90% by weight thereof.

7. A thermally diffusible composite according to claim 1 or 3, wherein the thermally diffusible medicine is in the form of an at least 2 mm thick porous carrier impregnated therewith.

8. A thermally diffusible composite according to claim 1 or 3, wherein the thermogenic composition further comprises (C) a filler.

9. A thermally diffusible composite according to claim 8, wherein the component (C) is at least one member selected from the group consisting of natural fibers, synthetic fibers, synthetic resin foam fragments, silica powder, porous silica gel, sodium sulphate, barium sulphate, iron oxides and aluminum oxide.

10. A thermally diffusible composite according to claim 8, wherein the thermogenic composition contains the filler (C) in a ratio by weight of 20/80–70/30 between the component (C) and the total of the components (A) and (B).

11. A thermally diffusible composite in enclosed state, comprising:
   (1) a thermally diffusible medicine for expelling or exterminating noxious organisms,
   (2) a thermogenic composition as the heat source for said thermally diffusible medicine, comprising
   (A) at least one member selected from the group consisting of sulphides, polysulphides and hydrosulphides of alkali metals, and hydrates thereof,
   (B) at least one member selected from the group consisting of carbonaceous material, iron carbide and activated clay and
   (3) an oxygen-impermeable container enclosing the diffusible medicine (1) and the thermogenic composition (2).

12. A thermally diffusible composite in enclosed state according to claim 11, wherein the thermally diffusible medicine is a thermally diffusible insecticide, attractant, repellent, rodenticide or fungicide.

13. A thermally diffusible composite in enclosed state according to claim 11 or 12, wherein the diffusible medicine (1) is carried on one side of a sheet-like substrate and the thermogenic composition (2) on the reverse side thereof and the whole is enclosed in the oxygen-impermeable container.

14. A thermally diffusible composite in enclosed state according to claim 11 or 12, wherein the alkali metal is at least one member selected from the group consisting of sodium and potassium.

15. A thermally diffusible composite in enclosed state according to claim 11 or 12, wherein the carbonaceous material is at least one member selected from the group consisting of carbon black, activated carbon, charcoal, coke, pitch, asphalt, graphite and soot.

16. A thermally diffusible composite in enclosed state according to claim 11 or 12, wherein the thermogenic composition contains the component (A) in an amount of 10–90% by weight thereof.

17. A thermally diffusible composite in enclosed state according to claim 11 or 12, wherein the thermally diffusible medicine is a pyrethroid type one.

18. A thermally diffusible composite in enclosed state according to claim 11 or 12, wherein the thermally diffusible medicine is in the form an at least 2 mm thick porous carrier impregnated therewith.

19. A thermally diffusible composite in enclosed state according to claim 11 or 12, wherein the thermogenic composition (2) further comprises a filler (C).

20. A thermally diffusible composite in enclosed state according to claim 19, wherein the filler (C) is at least one member selected from the group consisting of natural fibers, synthetic fibers, synthetic resin foam fragments, silica powder, porous silica gel, sodium sulphate, barium sulphate, iron oxides and aluminum oxide.

21. A thermally diffusible composite in enclosed state according to claim 19, wherein the thermogenic composition contains the filler (C) in a ratio by weight of 20/80–70/30 between the component (C) and the total of the components (A) and (B).

22. A thermally diffusible composite in enclosed state, comprising:
 (1) a thermally diffusible medicine for expelling or exterminating noxious organisms,
 (2) a thermogenic composition as the heat source for said thermally diffusible medicine, comprising
 (A) at least one member selected from the group consisting of sulphides, polysulphides and hydrosulphides of alkali metals, and hydrates thereof and
 (B) at least one member selected from the group consisting of carbonaceous material, iron carbide and activated clay,
 (3) an oxygen-impermeable container having an opening, which encloses the thermogenic composition (2) therein and onto which the thermally diffusible medicine (1) is attached in the form of a layer,
 (4) a filter provided on the container (3) to cover said opening, the filter preventing passage of the thermogenic composition therethrough from the container (3) and being permeable to oxygen, and
 (5) a member made of an oxygen-impermeable material airtightly covering said filter-covered opening.

23. A thermally diffusible composite according to claim 22, wherein the thermally diffusible medicine is a thermally diffusible insecticide, attractant, repellent, rodenticide or fungicide.

24. A thermally diffusible composite according to claim 22 or 23, wherein the alkali metal is at least one member selected from the group consisting of sodium and potassium.

25. A thermally diffusible composite according to claim 22 or 23, wherein the carbonaceous material is at least one member selected from the group consisting of carbon black, activated carbon, charcoal, coke, pitch, asphalt, graphite and soot.

26. A thermally diffusible composite according to claim 22 or 23, wherein the thermogenic composition contains the component (A) in an amount of 10–90% by weight thereof.

27. A thermally diffusible composite according to claim 22 or 23, wherein the thermally diffusible medicine is a pyrethroid type one.

28. A thermally diffusible composite according to claim 22 or 23, wherein the thermally diffusible medicine is in the form of an at least 2 mm thick porous carrier impregnated therewith.

29. A thermally diffusible composite in enclosed state according to claim 22 or 23, wherein the oxygen-impermeable container or molding is one made of an aluminum or steel foil or plate.

30. A thermally diffusible composite in enclosed state according to claim 22 or 23, wherein the oxygen-impermeable container is one made of steel.

31. A thermally diffusible composite according to claim 22 or 23, wherein the thermogenic composition further comprises (C) a filler.

32. A thermally diffusible composite according to claim 31, wherein the component (C) is at least one member selected from the group consisting of natural fibers, synthetic fibers, synthetic resin foam fragments, silica powder, porous silica gel, sodium sulphate, barium sulphate, iron oxides and aluminum oxide.

33. A thermally diffusible composite according to claim 31, wherein the thermogenic composition contains the filler (C) in a ratio by weight of 20/80–70/30 between the component (C) and the total of the components (A) and (B).

34. A thermally diffusible composite in enclosed state, comprising:
 (1) a thermally diffusible medicine for expelling or exterminating noxious organisms,
 (2) a thermogenic composition as the heat source for said thermally diffusible medicine, comprising
 (A) at least one member selected from the group consisting of sulphides, polysulphides and hydrosulphides of alkali metals, and hydrates thereof and
 (B) at least one member selected from the group consisting of carbonaceous material, iron carbide and activated clay,
 (3) an oxygen-impermeable container having an opening, which encloses the thermogenic composition (2) therein and onto which the thermally diffusible medicine (1) is attached in the form of a layer,
 (4) a filter provided on the container (3) to cover said opening, the filter preventing passage of the thermogenic composition therethrough from the container (3) and being permeable to oxygen, and
 (5) a member made of an oxygen-impermeable material airtightly enclosing the whole of the medicine (1)-attached container therein.

* * * * *